Figure 1:
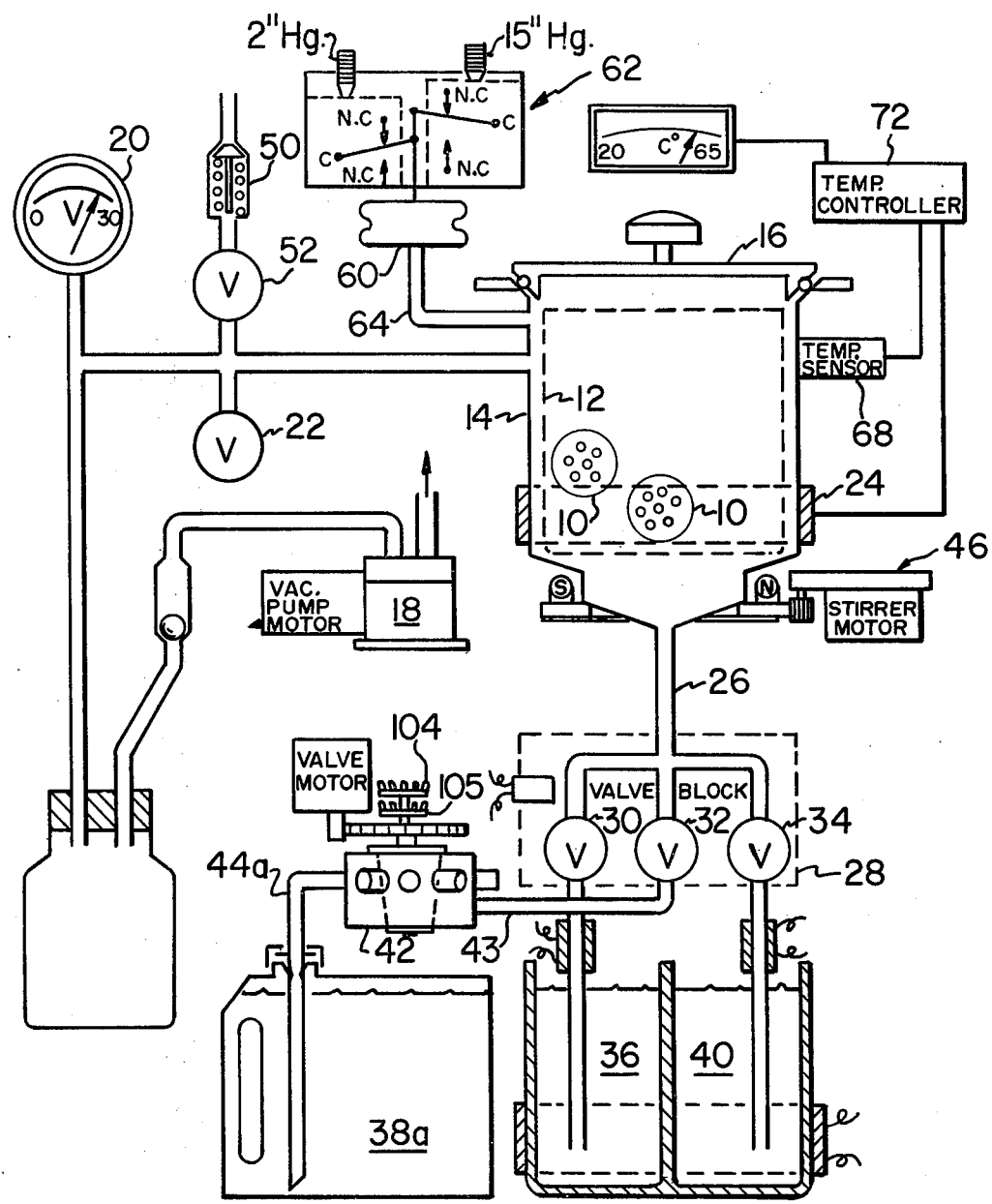

United States Patent [19]

Louder et al.

[11] 4,141,312

[45] Feb. 27, 1979

[54] APPARATUS FOR HISTOLOGICAL TISSUE PROCESSING

[75] Inventors: Nevitt M. Louder; Carlo E. Cuomo, both of Verona, Pa.

[73] Assignee: Fisher Scientific Company, Pittsburgh, Pa.

[21] Appl. No.: 797,366

[22] Filed: May 16, 1977

[51] Int. Cl.² ............................................. G01N 1/30
[52] U.S. Cl. ........................................ 118/7; 118/11; 118/50; 23/230 B; 134/95; 134/103; 422/67; 422/99
[58] Field of Search ................. 23/253 R, 259, 230 B, 23/230 R, 253 A; 195/127; 118/50, 7, 11, 5; 134/76, 85, 95, 99, 102, 103

[56] References Cited

U.S. PATENT DOCUMENTS

| | | | |
|---|---|---|---|
| 2,853,084 | 9/1958 | Lipshaw | 134/76 |
| 3,227,130 | 1/1966 | Weiskopf | 134/95 |
| 3,446,423 | 5/1969 | Carroll | 137/565 |
| 3,557,077 | 1/1971 | Brunfeldt et al. | 23/253 A |
| 3,604,436 | 4/1969 | Lipshaw | 134/76 |
| 3,725,010 | 4/1973 | Penhasi | 23/253 R |
| 3,762,362 | 10/1973 | Lipshaw | 118/5 |
| 4,003,708 | 1/1977 | Taguchi et al. | 23/253 R |

OTHER PUBLICATIONS

Fisher Scientific Product Bulletin, 6-370, (1964).
Lipshaw Catalogue No. 73, Lipshaw Manufact. Corp., Detroit, Mich., pp. F1-F6, (1973).

Primary Examiner—R.E. Serwin
Attorney, Agent, or Firm—Webb, Burden, Robinson & Webb

[57] ABSTRACT

This invention relates to apparatus for processing histological tissue specimens and the method of processing the specimens utilizing the apparatus. More particularly, the apparatus provides means for automatically processing the specimens in a single container by sequentially introducing and removing solvents and/or paraffin into and from said container.

12 Claims, 3 Drawing Figures

APPARATUS FOR HISTOLOGICAL TISSUE PROCESSING

Preparatory to sectioning, mounting and staining a tissue specimen for microscope examination in a laboratory, a histological tissue specimen is subjected to processing comprising treating the specimens, in appropriate sequence, with fixing, dehydrating, clearing and embedding agents. In a typical processing operation, specimens are subjected to (1) a fixing agent comprising a preferred solution of 10% Formalin in water; (2) a dehydrating agent comprising, in a plurality of stages, increasing concentrations, e.g. from 80–100% denatured alcohol; (3) a clearing agent comprising xylene or toluene, which are wax and alcohol soluble; and (4) an appropriate embedding agent, such as a paraffin wax.

Available apparatus for carrying out the aforementioned processing steps typically comprise a circular arrangement of reagent baths and a carriage for transporting a perforated basket containing specimens into and out of the baths and, finally, into molten paraffin. One shortcoming of such apparatus is that the carriage is actuated by electrically powered mechanical mechanisms. In the event of either or both electrical power failure or mechanical breakdown, loss of the entire specimen load may result through exposure of tissues to atmosphere for sufficient time to permit drying of the tissues.

The present invention is a histological tissue processor in which, contrary to prior art tissue processors, there is provided a single container, for holding tissue specimens to be processed, means for selectively subjecting the specimens to treating agents or fluids in the container and means for controlling the type of treating fluids to which the specimens are subjected and the duration of the treatment. The method of processing such specimens, using the processor, also forms a part of the invention.

The tissue processor, according to the invention, incorporates a pressure controlled means for controlling the flow of liquid into and out of the container comprising a vacuum source for the chamber, valve means for controlling the flow of liquid into the chamber and control means, such as a diaphragm and control circuit, responsive to the pressure into the chamber for controlling the operation of the vacuum source and the valve means.

The tissue holding container is adapted to be sealed against the atmosphere. The container has, in a preferred embodiment, a common inlet and gravity drain port. Stirrer means, preferably magnetically driven, are also provided. Means, such as electrical resistance bands, are associated with the container and other parts for heating them.

The histological tissue processor according to this invention exhibits a number of significant advantages over prior processors. The present tissue processor has increased capacity. While prior art processors generally hold from between about 35 to 100 tissue specimens, the processor of the invention has a capacity of about 105 to 300 specimens or 2 to 3 times the prior art capacity. The tissue processor of the invention permits use of controlled vacuum over the solvent baths and/or on paraffin wax impregnation bath if and as desired. This capability was not available with prior tissue processors. Similarly, in the present invention, the solvent can be subjected to controlled heat, if desired, and then only in the tissue chamber. This was not possible in prior processors. Safety thermostats may be incorporated in all automatic heating circuits.

The processing system employed in the tissue processor according to the invention maybe totally enclosed. Therefore, there is no possibility of tissue destruction resulting from electrical power or mechanical failure. Nor is the operator subject to noxious materials for lengthy time periods. In the use of automatic control of the processing system, the tissue processor of the invention permits selection or by-pass of one or more solvents without physical removal of the solvents from the processor. This selectivity is not available in known commercial tissue processors.

Commencement of the tissue processing in the processor in accordance with the invention may be delayed for a substantial time period, for example, preferably up to 60 hours. Each of the processing solvent stations may also be individually time programmed, preferably for periods up to four hours. It is not necessary for an operator to be in attendance with the processor at the end of a cycle. The tissue specimens will not be removed from the last bath except by manual command. In a preferred embodiment, each important condition of operability is shown by a light or dial indicator connected to solid-state program and control circuits for the tissue processor.

Figure 2:
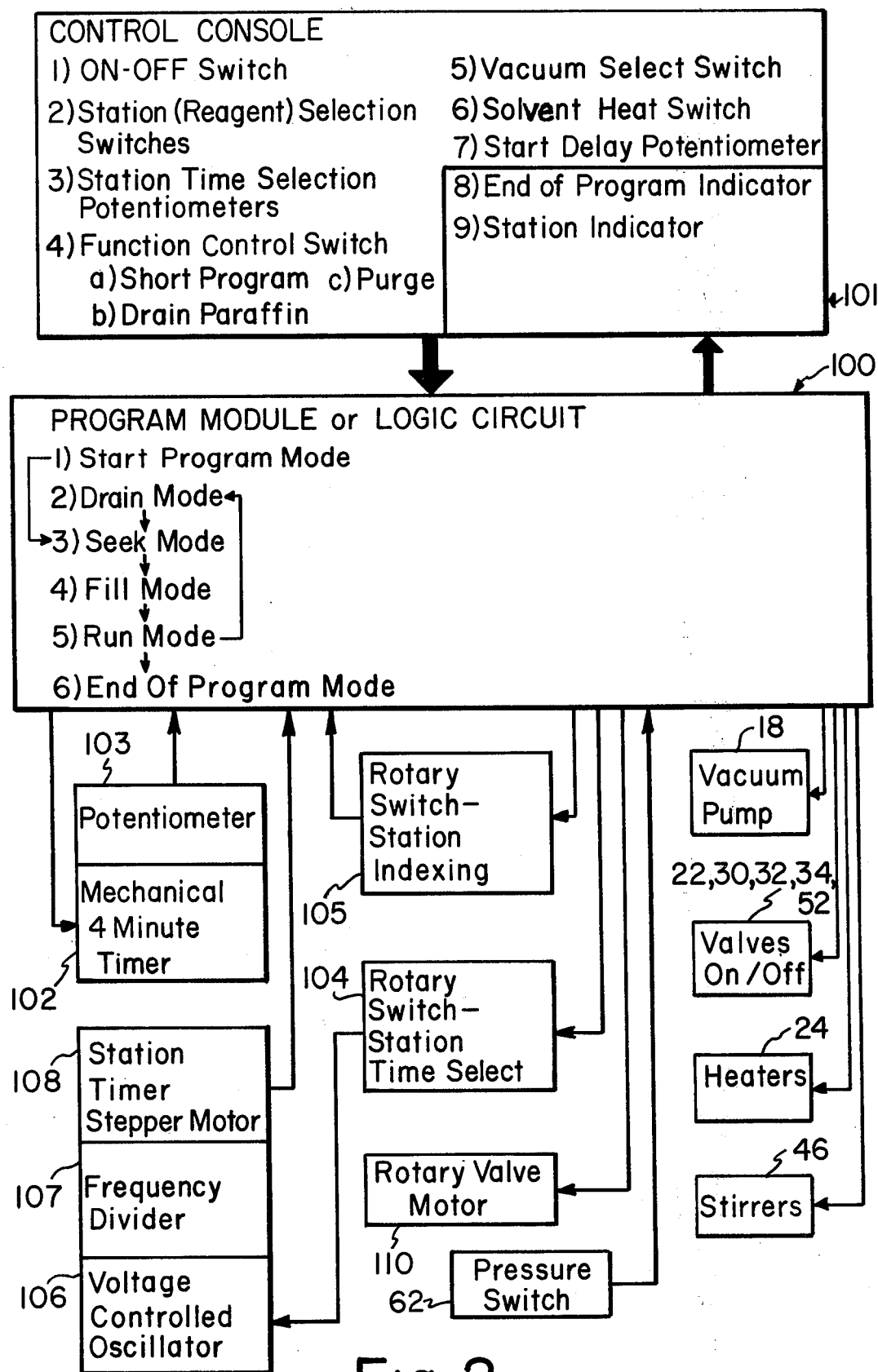
Figure 3:
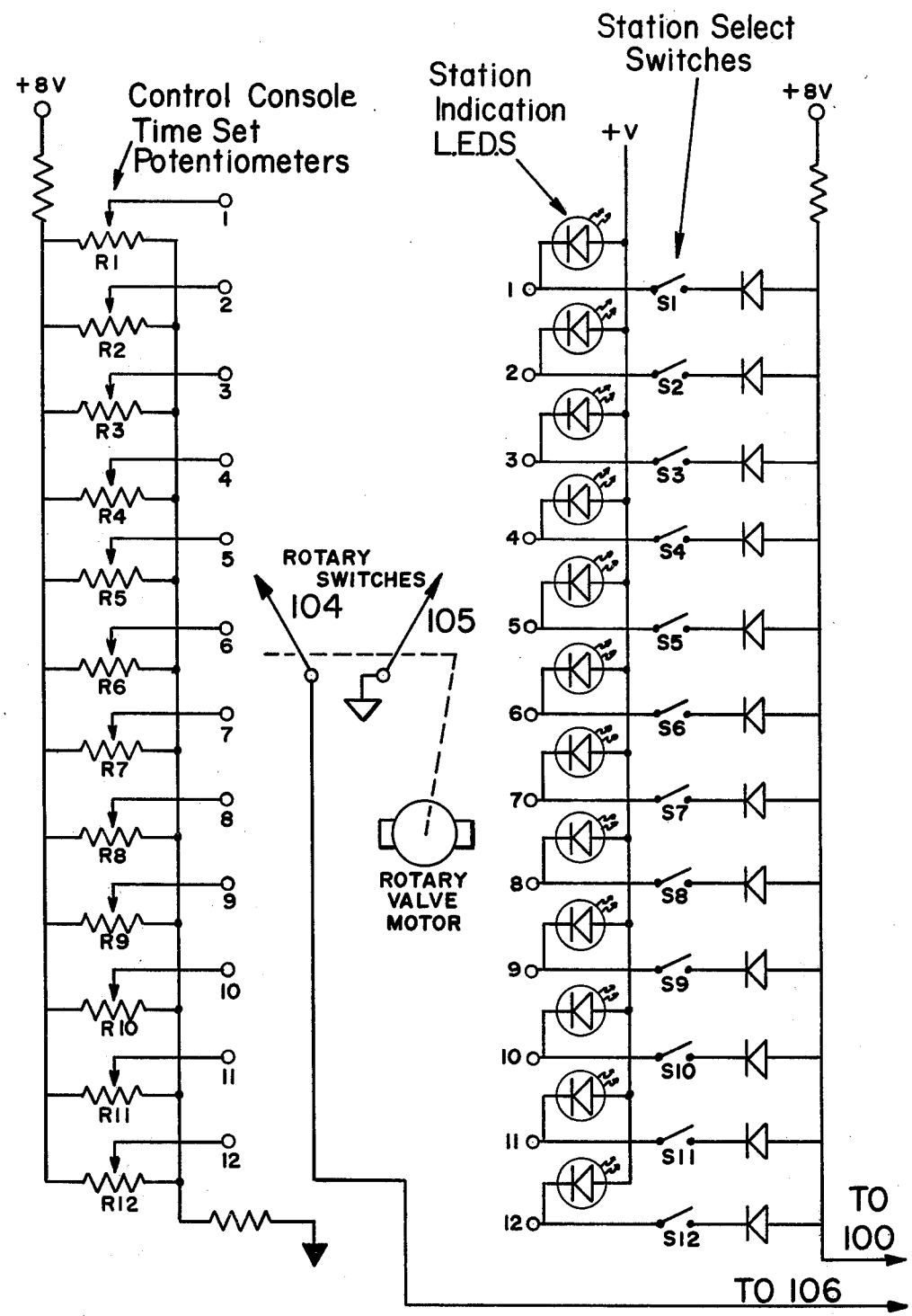

Further features and other objects and advantages will become apparent from the following detailed description made with reference to the drawings in which FIG. 1 is a schematic diagram of an apparatus according to the invention, FIG. 2 is a schematic block diagram for explaining the control of the apparatus according to the invention, and FIG. 3 is a wiring diagram useful for explaining the control console shown in FIG. 2.

The tissue processor according to the invention processes histological tissue specimens through fixing, dehydrating, clearing and embedding agents automatically. Referring to the schematic diagram of FIG. 1, tissue capsules 10 are randomly placed in a perforated tissue basket 12 and the basket is positioned in a tissue container 14. The container is closed and sealed by lid 16. A simple "O" ring seal may be used to insure a vacuum tight fit.

The tissue container 14 is plumbed to a vacuum pump 18, a vacuum gauge 20 and to a vacuum exhaust valve 22. A heater, such as band type heater 24 is provided for the container 14. An inlet and drain port 26 located in the bottom of the container 14 is in fluid communication via valve block 28 which includes solenoid operated valves 30, 32 and 34 with a first paraffin bath 36, a plurality of solvent baths 38a, 38b, 38c, . . . etc. and a second parafin bath 40.

Each solvent bath is in fluid communication with solvent valve 32 by means of a rotary valve 42. Valve 42 is a multiple port valve having a common port 43 sequentially coupled to, say twelve, selectable ports (44a, 44b, 44c, . . . etc.). Preferably, the selectable ports are radially extending in a fixed valve body and connectable with the common port by a rotating slide. Ten of the ports, for example, are plumbed to ten solvent baths and a remaining port is plumbed to a fitting (not shown) for purging or flush purpose. When the solvent value 32 is open, the tissue container 14 and the tissue capsule 10 contained therein are connected to one of the ten solvent baths selected by the rotary valve 42. Similarly, when valves 30 and 34 are open, the tissue container 14 and the tissue capsules contained therein are connected, in turn, to the paraffin baths 36 and 40.

The tissue processor is, in the preferred embodiment, controlled by a programming module 100, which determines the sequence and timing of all processing operations. Generally speaking, the operation of the tissue processor according to the invention may be summarized as follows: Tissue specimens to be processed are placed in a container sealed against atmosphere. The specimens are selectively subjected to treating agents or fluids introduced into the container. In a preferred embodiment of the invention, the rotary valve rotates to a first selected solvent bath, usually a fixation bath. Solvent valve 32 opens and vacuum pump 18 is energized causing the solvent (treating agent) to enter the container until all of it is transferred from the solvent bath, at which time the solvent valve 32 closes and the pump 18 is de-energized. The solvent is preferably stirred gently by a stirrer 46 magnetically driven from outside the container, thus moving it among the tissue capsules. When the first bath cycle is completed, the solenoid operated vacuum exhaust valve 22 is opened to amtosphere and the solvent valve 32 reopens permitting the solvent to drain via gravity into the solvent bath. The same cycle is repeated through each of the solvent baths selected by the rotary valve 42. For the paraffin bath cycles, molten paraffin flows from the heated paraffin baths 36, 40 through valves 30 or 34, respectively, and into the tissue container 14 which is heated to a preset temperature.

If desired, vacuums may be applied to the tissue container 14 during all bath cycles or during the paraffin bath cycles only. If desired, a low level, preset temperature may be applied to the tissue container 14 during all the solvent bath treatments. In any event, the container 14 and valve block 28 are preheated and maintained at an appropriate temperature prior to and during the paraffin treatment.

The specific functioning of above described tissue processor and the program module to control the various components of the tissue processor including valves, pumps and heaters may be understood by reference to FIG. 2 which is a schematic diagram and FIG. 3 which is a partial wiring diagram.

Preselected inputs to the programming module 100 are made by a control console 101 which is arranged to permit ready selection of the selectable operating conditions and additionally provides indication of mode and station at any given instance. The control console typically contains the master on-off switch and a FUNCTION CONTROL switch which enables selection of the automatic processing mode (START PROGRAM), and two manually selectable modes (DRAIN PARAFFIN and PURGE). The console contains, for example, twelve station (solvent) select switches $S_1$ to $S_{12}$ (see FIG. 3) which enables the tissue processor to treat the specimen, on a one at a time basis, with any of ten solvents and two paraffins as explained above. If a given station switch is off the corresponding station is bypassed and the specimen is not treated with the solvent available at that station. The control console also contains twelve station time select potentiometers $R_1$ to $R_{12}$ (See FIG. 3) which enable the time at any station to be adjusted between several minutes and four hours. The outputs of the station select switches and potentiometers are not directly applied to the programming module. Each set of outputs is selectively applied through rotary switches 104 and 105 (one for each set). The rotary switches are mechanically fixed to rotate with the rotary slide of valve 43 described above. Preferably, the rotary switches comprise one two-deck rotary switch. The remaining available selections that are made upon the control console 101, corresponding to preselected inputs to the programming module 100, will be described later in this specification.

The programming module or logic circuit 100 is basically a "hardwired computer," preferably using CMOS logic units. The program module commands certain outputs be delivered to the vacuum pump 18, valves 22, 30, 32, 34 and 52, heater 24, stirrer 46 and rotary valve 42 for desired operating modes of the tissue processor. When the FUNCTION CONTROL switch on the consol is turned to the START PROGRAM mode an input to the logic circuit of the programming module starts the automatic operation of the tissue processor. The tissue processor advances through DRAIN, SEEK, FILL and RUN modes as defined by the following table.

| MODE | | VACUUM EXHAUST VALVE | VACUUM PUMP | SOLVENT VALVE | PARAFFIN VALVE | ROTATING VALVE MOTOR | MAGNETIC STIRRER | HEATERS |
|---|---|---|---|---|---|---|---|---|
| DRAIN | | | | | | | | |
| | Solvent Station | OPEN | OFF | OPEN | CLOSED | OFF | OFF | — |
| | Paraffin Station | OPEN | OFF | CLOSED | OPEN | OFF | OFF | ON |
| SEEK | | —* | OFF | CLOSED | CLOSED | ON | — | — |
| FILL | | | | | | | | |
| | Solvent Station | CLOSED | ON | OPEN | CLOSED | OFF | ON | — |
| | Paraffin Station | CLOSED | ON | CLOSED | OPEN OFF | ON | ON | — |
| RUN | | | | | | | | |
| | Solvent Station | CLOSED | OFF or ON - OFF | CLOSED | CLOSED | OFF | ON | — |
| | Paraffin Station | CLOSED | OFF or ON - OFF | CLOSED | CLOSED | OFF | ON | ON |

*dash means operating condition is not important to mode definition.

Prior to explaining the tissue processor operation in detail, two automatic inputs to the program module should be understood. At the completion of any given solvent treatment, the tissue processor is advanced through DRAIN, SEEK, FILL and the initiation of the RUN mode. This may be accomplished in about four minutes. A mechanical timer 102 is activated just prior to the DRAIN mode. The timer is simply an AC timing motor that makes one revolution in, say, four minutes (clearly other rotation times could be selected). The motor turns a 2000 ohm potentiometer 103. The wiper of the potentiometer thereby provides a steadily increasing output voltage which is compared in the control logic to preset threshold levels at which levels, outputs command the advance from DRAIN to SEEK to FILL to RUN modes. An important feature of this timer system is the ability to resume operation of the tissue processor at exactly the same instant in the process after a shutdown, either intentionally caused by the operator or accidently caused, say by power failure. Electronic timers and memories would go blank with a shutdown resulting in confusion upon restart.

Once the tissue processor has stopped at a preselected station and filled the tissue or specimen container with a solvent, it is necessary to provide accurate preselected hold times at each processing station. For this the tissue processor utilizes a potentiometer adjusted time circuit. The twelve time-set potentiometers $R_1$ to $R_{12}$ on the control console (already described) provide a voltage, proportional to time, via a rotary switch 104 to a voltage controlled oscillator 106. The voltage controlled oscillator provides output pulses whose frequency are inversely proportional to the voltage input, to a frequency divider. The frequency divider divides the pulses by a constant number and supplies the resulting frequency pulses to a stepper motor or station timer 108. This motor completes one revolution for a set number of drive pulses and depending upon the frequency of the applied pulses, one revolution can take from several minutes to several hours, say from 10 minutes to 4 hours. Upon a complete revolution, this motor 108 causes a switch to close outputing a signal to the logic circuit indicating that the processing period is completed.

With the initiation of the START PROGRAM mode by the FUNCTION CONTROL switch on the control console, the logic circuit enters the SEEK mode and outputs a signal to the rotary valve motor such that the slide of the rotary valve 43 rotates from station no. 12 (the last station) to station no. 1 (the first station) and will stop at station no. 1, if and only if, the station select switch for that station ($S_1$) has been closed. If not, the valve will continue to rotate to station no. 2 and so forth seeking out the first station having a corresponding station select switch closed. As already explained, turned with the slide of rotary valve 43 are rotating switches 104 and 105. Upon reaching a new station, the rotary indexing switch 104 will output a station indexing signal to the logic circuit, if the corresponding station select switch has been preselected closed.

Assuming station no. 1 has been preselected by the station select switch $S_1$ and has been programmed for time by potentiometer $R_1$, say 1 hour, the slide of the rotary valve will stop at station no. 1. The control logic is advanced from the SEEK mode to the FILL mode (as explained above by signals outputed from the four minute timer 102 and corresponding potentiometer 103) and now directs the filling function. Solvent valve 32 is directed to open and the vacuum pump 18 is turned on. Thus, reagent is drawn from the reservior corresponding to station no. 1 through the solvent valve 32 into the container 14. It is essential that the container 14 fill at a controlled rate. A vacuum of approximately two inches mercury will limit the amount of boiling agitation that occurs when the contents of the solvent container are emptied and air enters the tissue container through the snorkel and valve 32. Boiling agitation is particularly unwelcome when transporting molten paraffin, whereupon the paraffin splashes onto the lid or worse enters the vacuum port in the container wall. The two inches of mercury pressure is controlled by a relief check valve 50 (see FIG. 1). This is simply a spring loaded check valve with access to the atmosphere. When the pump is operating in the FILL mode, vacuum, say in excess of two inches mercury, is relieved from the container by the admission of air through the check valve. Valve 52, which is a normally closed solenoid valve, opens only on the operation of the pump during the FILL mode. The magnetic stirrer is actuated at the start of the FILL mode.

The FILL mode may be ended when the entire contents of a solvent container have been drawn into the specimen container 14. To enable the immediate termination of the FILL mode at this point, without waiting for the four minute timer 102 to advance the logic circuit to the next mode, a pressure switch 62 senses the drop in vacuum in the container 14 caused by air drawn into that container through valve 32. The switch 62 signals the logic circuit to advance immediately to the RUN mode thereby shutting down the vacuum pump and closing valves 32 and 52.

The electronic control logic is advanced to the RUN mode by the four minute timer 102 if not already advanced to that mode by the complete filling of the specimen container. The control logic remains in the RUN mode until the station timer 108 has completed one revolution as above described. At that time, a switch is closed outputing a signal to the programming module that the RUN mode is completed and the mechanical four minute timer 102 is actuated advancing the logic circuit to the DRAIN mode. In this instance, when the one hour program for station no. 1 has elapsed, the four minute timer is reset and in turn directs the control logic to the DRAIN mode; thereby opening the vacuum exhaust valve 22 and the solvent control valve 32. This enables the solvent to retrace its path through the rotary valve to the solvent container assigned thereto. During draining, the magnetic stirrer is stopped as it has been demonstrated that more thorough draining is achieved with the stirrer idle. Both the vacuum exhaust valve and the solvent control valve remain open for two minutes. This has been found to be ample time for the tissue container solvent to return to its original reservoir. Typical two liter solvent drain time is about 65 seconds plus or minus 10 seconds. At the end of the two minutes, the two valves 22 and 32 are closed and the magnetic stirring resumes.

The electronic control logic is advanced by the four minute timer 102 to the SEEK mode and the logic circuit signals the rotary valve motor to advance to the next station on which time has been programmed, in other words, to advance to the next station for which the corresponding station selection switch has been closed and the station time selection potentiometer has been adjusted. Thereafter, FILL, RUN, DRAIN and SEEK modes are continued until the end of the RUN mode for the last station (station no. 12). Conclusion of the RUN mode for the last station does not initiate the four minute timer 102 and the DRAIN mode.

The molten paraffin contained in the baths nos. 36 and 40 are drawn into the tissue container when the rotary valve is at the final stations 11 and 12 but not through the rotary valve. The paraffin baths heated, for example, by two 75-watt heaters may be controlled at a preset temperature of about 64°. Two copper tubes leading from the paraffin valves 30 and 34 are immersed in the paraffin baths. They may be individually heated by 10-watt wrap-around heaters not controlled by thermostats. These tube heaters are always energized to serve to faciliate the flow of paraffin as required.

The valve block 28 is the physical mounting gallery for the valves 30, 32 and 34, and a common access port to the tissue container 14. In view of the molten paraffin requirements, the valve block 28 and specimen container 14 are heated when required. The 150-watt cartridge heaters, for example, may be thermostatically controlled to heat the valve block to about 64° C. Band type heaters 24 serve to heat the specimen container.

When the rotary valve is advanced to the station no. 11 upon which time has been programmed, or station no. 12 (the final station) upon which time has or hqas not been programmed, the rotary valve will stop at the appropriate position and await the FILL mode. The control logic will direct that heat be applied to the valve block 28 and to the tissue container 14 at this time. For the next two minutes (approximately) the heat will rise in both areas. The tissue container will achieve a control preset temperature of about 60° C. established by a temperature controller.

When the valve block and tissue or specimen container temperature reaches the thermostat set point of about 64° C., the programmer opens the appropriate paraffin valve 30 or 34 and valve 52. The vacuum pump 18 is turned on and controlled by the two inches of mercury relief check valve, draws molten paraffin into the tissue container and, as described before, when air enters the specimen container, the switch 62 stops the pump and denergizes normally closed solonoid valves 52 and 30 or 34, which ever applies. The molten paraffin will remain sealed and stirring for the prescribed programmed time.

When the allocated time is elapsed for the paraffin bath, the control logic then directs the DRAIN mode if in station no. 11. Valve 22 opens exhausting the vacuum contained in the system. A few seconds later the magnetic stirrer stops and the paraffin drain valve 30 reopens. The paraffin drains into the heated bath. Again an ample two minutes is assigned for the drain time although one minute is a typical drain time. The extra one minute does allow thorough drain except for residuals.

The rotary valve then advances to the twelfth and last station. The paraffin infiltration FILL mode at station no. 12 is identical to that at station no. 11. However, the valve block and tissue container are already at the fill temperature. There is no hesitation, therefore, in the filling sequence at station no. 12 as had occurred at station no. 11.

The control logic does not initiate the draining at the last paraffin station. When the time programmed for station no. 12 has timed-out, the control logic signals the operator by turning on the "END OF PROCESS" panel light on the control console. The processing is now complete and awaits the operator's convenience to unload the tissue basket. The operator rotates the FUNCTION CONTROL switch to the "DRAIN PARAFFIN" mode. This signals the control logic to direct a normal paraffin drain sequence as described above.

Following the unloading of the tissue container it is recommended that the residual paraffin film be removed from the walls and from the valve block. The rotary valve 43 has no connections to the radial ports at the eleventh and twelfth stations. At the twelfth station, however, there is an exhaust port connecting to a conduit which may be directed to a refuse container. At the end of the drain caused by the function control switch being set to DRAIN PARAFFIN, the valves in the valve block are all closed. A clearing agent may then be poured into the tissue container 14 by removing the lid. The function control switch is then turned by the operator to PURGE. In this mode, the solvent valve 32 is opened allowing the clearing agent to drain through the rotary valve out the exhaust port associated with the twelfth position. The magnetic stirrer is stopped during draining to promote good draining as already explained.

It is an advantage according to this invention that a vacuum may be applied to the tissue container at the operator's discretion during the RUN mode by setting the vacuum control switch on the control console to either ALL STATIONS or PARAFFIN ONLY. (In the ALL STATIONS position, vacuum is applied in solvent treatment steps as well as the paraffin treatment steps. In the PARAFFIN ONLY position, vacuum is only provided when in the eleventh and twelfth stations.) Controlled vacuum (15 inches of mercury) is available for this event and will occur when desired at the completion of the FILL mode. The vacuum pump is energized at approximately one minute following completion of a FILL mode. A vacuum gauge 20 will indicate, say 15 inches of mercury, vacuum in approximately 15 seconds. At this point the vacuum control switch 62 will switch off the pump. The vacuum control switch assumes control of the pump in maintaining the preset vacuum. The pump cycle frequency varies depending upon solvent volatility, temperature and agitation upon filling. Although the vacuum pump has its own check valve, as shown in FIG. 1, an all glass check valve may be added as a security backup. Also, a glass bottled trap may be installed as shown in FIG. 1 as a conventional part of the vacuum system.

The temperature of the tissue container 14 may be controlled by a solid-state circuit with a thermistor sensor 68 and two 100-watt wrap-around heaters 24. The temperature may be adjustably set at controller 72 between ambient (we can only apply heat) and 65° C. This temperature may be maintained throughout all solvent treatment steps, when the SOLVENT HEAT switch on the control consol 101 is switched ON. Otherwise, as explained above, the container 14 is only heated during the paraffin stage treatments.

The operator may delay the start of processing up to 60 hours by adjustment of a START DELAY potentiometer on the control consol 101. When switched to the START PROGRAM, after a start-delay has been entered, the processing function will be initiated. Reagent in the first station having a preset timer indication will be pulled into the tissue container. This will occur independent of any preset delay time. The time the first processing reagent spends in the tissue container will be the total of the preset delay time plus the set time indicated on the associated timing control potentiometer. If the delay timer has not been set, only the time set on the timing control will be in effect.

Having thus described my invention with the detail and with the particularly required by the Patent Laws, what is desired protected by Letters Patent is set forth in the following claims.

We claim:

1. Apparatus for processing histological tissue specimens comprising:
   (a) a vacuum tight container for specimens and treating fluids having a removable cover for unencumbered placement of specimens in the container, said container having a single opening for inlet and drain at the bottom thereof,
   (b) first and second valves in communication with the inlet and drain opening in the container,
   (c) a container for warm impregnant or the like in communication with said first valve, (d) a third valve having a plurality of selectable ports and a common port connectable to any of said selectable ports, said common port in communication with said second valve, (e) a plurality of treating fluid containers in communication with said selectable ports on said third valve, (f) a vacuum pump in communication with said specimen container, (g) a vacuum exhaust valve in communication with said specimen container, (h) means for controlling the first, second and third valves, the vacuum pump and the vacuum exhaust valve to sequentially draw treating fluids into said specimen container and return the treating fluids to their respective containers, and finally to draw warm impregnant into said specimen container to treat histological tissue specimens.

2. An apparatus according to claim 1 in which said means for controlling comprises a logic circuit for producing sequential output signals placing the apparatus in DRAIN, SEEK, FILL and RUN modes, said DRAIN mode comprising one of said first and second valves open and said exhaust valve open, said SEEK mode comprising all of the first and second and exhaust valves closed and the step-wise movement of the third valve to the next position at which treating fluid is to be drawn or to the last station wherein impregnant is to be drawn, said FILL mode comprising opening one of said first and second valves and drawing a vacuum upon said container with the vacuum pump, said RUN mode comprising said first and second valves closed.

3. Apparatus according to claim 2 wherein said means for controlling comprises an electronic logic circuit and first and second mechanical timers, said first timer being a short-term timer activated at the end of a RUN mode to output a sequence of signals moving the tissue processor through the DRAIN, SEEK, FILL and initiation of the next RUN mode and a second timer being a long-term timer for holding the tissue processor in the RUN mode for a period of time to allow treatment of the histological tissues in the container and, thereafter, for activating the first timer and its corresponding sequence.

4. An apparatus according to claim 1 further comprising a vacuum limit valve for limiting the vacuum drawn on the container during a FILL mode to less than about two inches of mercury.

5. An apparatus according to claim 2 further comprising means for sensing loss of vacuum during the FILL mode and signaling the means for controlling such that it immediately advances the apparatus to the RUN mode.

6. An apparatus according to claim 3 further comprising means for sensing loss of vacuum during the FILL mode and signaling the means for controlling such that it immediately advances the apparatus to the RUN mode.

7. Apparatus according to claim 2 further comprising means for heating the specimen container which means is automatically actuated prior to drawing impregnant into said container and as long as impregnant is in said container.

8. Apparatus according to claim 3 in which the first timer and its corresponding sequence are not initiated at the time when the second timer times out for the last station and means are provided for manually initiating a DRAIN PARAFFIN mode opening the second valve and vacuum exhaust valve.

9. An apparatus according to claim 8 wherein means are provided for draining cleaning agents from the tissue container by manually initiating a PURGE mode in which the first valve and vacuum exhaust are opened and the third valve is arranged with the common port in communication with a selectable valve port connected to a waste spigot.

10. An apparatus according to claim 2 further comprising a timer for holding the apparatus in a START DELAY mode in which, after the first solvent is drawn into the tissue container, start of the apparatus is delayed for a preselected time.

11. An apparatus according to claim 2 further comprising means for activating and controlling the vacuum pump during a selected RUN mode to apply a vacuum over the treating fluid and/or impregnant baths which is greater than the vacuum drawn during the FILL mode.

12. An apparatus according to claim 2 further comprising a magnetically driven stirrer which stirrer is automatically activated as preselected but not during the DRAIN mode.

* * * * *